United States Patent [19]

Fache et al.

[11] Patent Number: 5,900,506
[45] Date of Patent: May 4, 1999

[54] METHOD OF PROCESSING REACTION MIXTURES OBTAINED FROM THE OXIDATION OF CYCLOHEXANE

[75] Inventors: Eric Fache, Caluire et Cuire; Philippe LeConte, Meyzieu; Gilbert Marin, Ste Foy-les-Lyon, all of France

[73] Assignee: R.P. Fiber & Resin Intermediates, Courbevoie Cedex, France

[21] Appl. No.: 08/990,184

[22] Filed: Dec. 12, 1997

[30] Foreign Application Priority Data

Dec. 12, 1996 [FR] France .................................. 96 15523

[51] Int. Cl.$^6$ ........................... C07C 51/42; C07C 55/02
[52] U.S. Cl. ........................... 562/593; 562/590; 562/543
[58] Field of Search .................................. 562/593, 590, 562/543

[56] References Cited

U.S. PATENT DOCUMENTS 3,607,926  9/1971  Smetana ................................. 260/533
4,052,441  10/1977  Brunner ................................. 560/179

FOREIGN PATENT DOCUMENTS 1266886  11/1961  France .
1477314  6/1967  France .
96/03365  2/1996  WIPO .

Primary Examiner—Gary Geist
Assistant Examiner—Rosalynd Keys
Attorney, Agent, or Firm—Burns, Doane, Swecker & Mathis, L.L.P.

[57] ABSTRACT

The present invention relates to a method of processing reaction mixtures obtained from the oxidation reaction of cyclohexane to adipic acid. The processing of the reaction mixture obtained from the direct oxidation of cyclohexane to adipic acid with oxygen, in an organic solvent and in the presence of a catalyst, comprises:

(a) a distillation which makes it possible to separate out, on the one hand, a distillate comprising at least some of the most volatile compounds such as the unconverted cyclohexane, the organic solvent, cyclohexanone, cyclohexanol, cyclohexyl esters, lactones and water, and, on the other hand, the distillation residue comprising the diacids formed and the catalyst;

(b) the addition of water to the distillation residue in order to form an aqueous solution;

(c) crystallization of the adipic acid from the aqueous solution of the distillation residue.

18 Claims, No Drawings

METHOD OF PROCESSING REACTION MIXTURES OBTAINED FROM THE OXIDATION OF CYCLOHEXANE

BACKGROUND OF THE INVENTION

1. Technical Field of the Invention

The present invention relates to a method of oxidation of cyclohexane to adipic acid, and more particularly to the processing of the reaction mixtures obtained from this oxidation reaction.

2. Description of the Prior Art

The direct oxidation of cyclohexane to adipic acid is a process which has been explored for a long time, in particular on account of the obvious advantages there would be in converting the cyclohexane into adipic acid in a single step and without using an oxidizing agent such as nitric acid, since this compound generates nitrogen oxides which need to be processed subsequently in order to avoid pollution.

Patent Application WO-A-94/07833 describes the oxidation of cyclic hydrocarbons into corresponding diacids, in a liquid phase containing a solvent, at a temperature of at least 60° C., using a gas containing oxygen and in the presence of an oxidation catalyst such as a cobalt compound, and points out that the solvent represents less than 1.5 mol per mole of cyclic hydrocarbon, that the said solvent comprises an organic acid having only primary or secondary hydrogen atoms and that the reaction is carried out in the presence of at least 0.002 mol of cobalt-based catalyst per 1,000 g of reaction mixture. At the end of the reaction, the diacid formed is isolated.

Patent Application W0-A-94/07834, filed on the same day as the one above, also describes the same process, but develops the phases of processing the final reaction mixture. This processing consists in separating out the diacid formed, by cooling the reaction mixture in order to cause the said diacid to precipitate out, in separating by filtration the diacid from two liquid phases, a non-polar phase which is recycled, and a polar phase which is also recycled after an optional hydrolysis and separation of an additional amount of diacid.

These patents present solutions which allow the one-step oxidation of cyclohexane to adipic acid with industrially acceptable selectivity, but they provide no solution which is industrially applicable to the processing of the reaction mixture obtained from the oxidation, taking into account the separation of the many different reaction products and side products, unconverted products and the catalyst.

SUMMARY OF THE INVENTION

The present invention provides a method of processing the reaction mixture obtained from the direct oxidation of cyclohexane to adipic acid with oxygen, in an organic solvent and in the presence of a catalyst, said method comprising:

(a) distilling said reaction mixture to provide (i) a distillate comprising at least some of the most volatile compounds in the reaction mixture (such as the unconverted cyclohexane, the organic solvent, cyclohexanone, cyclohexanol, cyclohexyl esters, lactones and water), and (ii) a distillation residue comprising the diacids formed and the catalyst;

(b) adding water to the distillation residue to form an aqueous solution; and (c) crystallizing the adipic acid from the aqueous solution of the distillation residue.

DETAILED DESCRIPTION OF BEST MODE AND SPECIFIC/PREFERRED EMBODIMENTS OF THE INVENTION

The organic solvent is, more particularly, one or more aliphatic carboxylic acids.

The catalyst preferably contains cobalt, manganese or a mixture of cobalt and manganese.

The distillation is carried out such that most and, as far as is possible, essentially all, of the unconverted cyclohexane and the solvent, in particular the carboxylic acid preferably used, are separated from the adipic acid.

The method thus allows, in particular because of the distillation of the solvent and more particularly of the carboxylic acid solvent, the crystallization of the adipic acid to be performed in water, this solvent having many advantages over other crystallization solvents such as acetic acid, for example. The reason for this is that as well as avoiding the subsequent, often difficult, elimination of traces of these solvents, the lower solubility of adipic acid in cold water also makes it possible to limit or even, if this is economically acceptable, to dispense with the production of a second crop of less pure adipic acid from the solutions derived from the first crystallization. In addition, in an industrial process, additional risks of corrosion of the apparatus, entailed by the prolonged presence of aliphatic carboxylic acid when this is used as solvent, are thus avoided.

The distillation step is generally carried out at a temperature of from about 25° C. to about 250° C. and at an absolute pressure of between about 10 Pa and atmospheric pressure. Preferably, the temperature of the mixture during the distillation will be maintained between about 70° C. and about 150° C.

The distillation can, if necessary, be carried out in several successive steps, in particular in the preferred mode in which it is desired to eliminate most, for example more than about 90% and even more than about 99%, of the solvent such as the aliphatic carboxylic acid.

Preferably, the reaction mixture obtained from the direct oxidation of cyclohexane into adipic acid undergoes an operation of settling into two liquid phases before the distillation step: an upper, substantially cyclohexane phase and a lower phase substantially comprising the solvent, such as an aliphatic carboxylic acid, the diacids formed, the catalyst and some of the other reaction products.

The cyclohexane phase is usually reintroduced into a cyclohexane oxidation operation, either directly or after optional processing consisting primarily in eliminating the water contained therein. This processing can consist in particular of an azeotropic distillation.

The lower phase is subjected to the distillation mentioned above.

An advantageous variant of the method of the invention consists in introducing water vapor into the reaction mixture before or during the distillation step. This operation can allow better entrainment of certain compounds present in the mixture subjected to distillation. It can also carry out a partial or total hydrolysis of the carboxylic esters which may also be found in the mixture for distillation.

The distillate obtained in the distillation operation described above comprises the various volatile compounds and water. These volatile compounds can be upgraded and are thus recycled into a further cyclohexane oxidation reaction, after an at least partial elimination of water by any known means, in particular by azeotropic distillation.

The water added to the distillation residue represents from about 0.01 to about 5 times the weight of the mixture obtained after said distillation. Preferably, the amount of water added represents from about 0.1 to about 3 times this weight.

One variant of the method according to the invention consists in carrying out a liquid/liquid extraction on the aqueous solution obtained above, before crystallizing the adipic acid.

This extraction is performed using a water-immiscible solvent or mixture of solvents. By way of examples of such solvents, mention may be made of aliphatic, cycloaliphatic or aromatic hydrocarbons such as, for example, hexane, cyclohexane, benzene and toluene, esters such as, for example, butyl acetate and cyclohexyl acetate, halogenated hydrocarbons such as, for example, trichloromethane and dichlorobenzenes, and ethers such as, for example, diisopropyl ether. Cyclohexane is preferably used, for its efficacy and so as not to complicate the process. In the context of an industrial process running continuously, all or part of the cyclohexane layer separated from the reaction mixture by settling may be used for this liquid/liquid extraction, before the distillation step. In the preferred case of the use of cyclohexane in order to carry out the extraction, the cyclohexane solution obtained is usually reintroduced into a cyclohexane oxidation operation, either directly or, preferably, after processing consisting primarily in eliminating the water contained therein. As above, this processing can consist in particular of an azeotropic distillation.

Another variant of the process consists in heating the aqueous solution obtained after addition of water to the distillation residue, so as to hydrolyze the esters which may still be present in this solution. The cyclohexanol formed by this hydrolysis is separated out by azeotropic distillation. This hydrolysis can be performed in the presence of a strong acid catalyst which is either dissolved, such as a protonic acid, or not dissolved, such as an acidic heterogeneous catalyst.

The crystallization of the adipic acid from the aqueous solution is carried out according to the usual techniques of crystallization. It can be followed by recrystallization of the adipic acid obtained if the purity of the latter is not considered to be sufficient for the intended applications.

The aqueous solution remaining after crystallization of the adipic acid still contains a certain amount of dissolved adipic acid, which can be recovered in a second crop after concentrating the said aqueous solution. It also contains the other diacids formed in minor amount during oxidation of the cyclohexane, primarily glutaric acid and succinic acid, which can be separated out by known techniques, and, lastly, the catalyst. The catalyst is generally recovered by liquid/liquid extraction or by membrane electrodialysis. The catalyst thus recovered is recycled in a further oxidation reaction of cyclohexane to adipic acid, after an additional amount has been added, if necessary.

The crude reaction mixture which is used in the method of the invention originates from the oxidation, which is known per se, of cyclohexane with a gas containing oxygen, in a liquid medium comprising an organic solvent, preferably a carboxylic acid, and in the presence of a catalyst, in particular a catalyst containing cobalt, manganese or a mixture of cobalt and manganese.

For the preparation of this crude reaction mixture, reference may be made to the methods described in the prior art, in particular in U.S. Pat. No. 2,223,493. Thus, the initial cyclohexane/carboxylic acid weight ratio can be, for example, between about 0.1/1 and about 10/1 and preferably between about 0.2/1 and about 4/1. The catalyst preferably comprises a cobalt compound which is soluble in the reaction medium, chosen, for example, from cobalt carboxylates (such as cobalt acetate tetrahydrate), cobalt chloride, cobalt bromide and cobalt nitrate and/or a soluble manganese compound chosen, for example, from manganese carboxylates (such as manganese acetate), manganese chloride, manganese bromide and manganese nitrate.

The amount of catalyst, expressed as a weight percentage of cobalt and/or of manganese relative to the reaction mixture, is generally between about 0.01% and about 5% and preferably between about 0.05% and about 2%, without these amounts being critical. However, an amount of catalyst having a sufficient activity should be used while not using excessively large amounts which will then need to be separated from the final reaction mixture and recycled.

Besides cobalt and manganese, the catalyst can also contain other compounds based on metals such as nickel and/or iron and/or copper and/or cerium and/or vanadium and/or hafnium and/or zirconium.

It is advantageous also to use a compound for initiating the oxidation reaction, such as, for example, a ketone or an aldehyde. Cyclohexanone, which is a reaction intermediate, is most particularly recommended. Generally, the initiator represents from about 0.01% to about 20% by weight relative to the weight of the reaction mixture used, without these proportions having any critical value. The initiator is especially useful when starting the oxidation and when cyclohexane is oxidized at a temperature below about 120° C. It can be introduced from the start of the reaction.

The carboxylic acid preferably used as solvent in the cyclohexane oxidation reaction is more particularly a saturated aliphatic carboxylic acid having from 2 to 9 carbon atoms and having only primary or secondary hydrogen atoms.

Acetic acid is preferably used as solvent for the cyclohexane oxidation reaction. In the present description, reference will occasionally be made, for the sake of convenience, to acetic acid as the carboxylic acid used in the various steps of the method.

The oxidation can also be carried out in the presence of water introduced from the initial stage of the method.

The cyclohexane oxidation reaction is generally carried out at a temperature of from about 60° C. to about 180° C. and preferably from about 70° C. to about 120° C.

The pressure is not a critical parameter of the reaction and is generally between about 10 kPa (0.1 bar) and about 10,000 kPa (100 bar).

In order to further illustrate the present invention and the advantages thereof, the following specific example is given, it being understood that same is intended only as illustrative and in nowise limitative.

EXAMPLE 1

A 1.5 liter titanium-jacketed autoclave fitted with a six-paddle turbomixer and various openings for introducing the reactants and the fluids or for removing the reaction products and the fluids, and which has been purged beforehand with nitrogen, is loaded at room temperature with:

(i) cobalt acetate tetrahydrate: 4.0 g (16 mmol)
(ii) acetic acid: 359 g (5.98 mol)
(iii) cyclohexane: 289.7 g (3.45 mol)
(iv) cyclohexanone: 3.2 g (32.7 mmol)

After closing the autoclave, the nitrogen pressure is brought to 20 bar, stirring is started at 1000 revolutions/min and the temperature is brought to 105° C. over 20 min. The nitrogen is then replaced by 20 bar of depleted air (5% oxygen). The inlet gas flow rate is adjusted to 250 liters/hour.

After an induction period of about 10 min, during which there is no consumption of oxygen, the temperature rises 2° C. to 3° C. and the consumption of oxygen commences. The oxygen titer of the air at the autoclave inlet is gradually increased to 21% as a function of the consumption by oxidation.

The oxygen titer at the reactor outlet remains less than 5% throughout the test. The temperature in the autoclave varies between 104.9° C. and 105.1° C.

When 50 liters of oxygen have been consumed (degree of conversion of the cyclohexane of about 20%), continuous injection of the liquid phase is commenced: injection of an acetic acid solution containing 1.1% by weight of cobalt acetate tetrahydrate at a flow rate of 3.7 ml/min and injection of cyclohexane at a flow rate of 4.1 ml/min. The liquid product is stored continuously in a 7 liter decanter at 70° C.

After 400 minutes from the start of the reaction, the air is gradually replaced by nitrogen and the contents of the autoclave are transferred into the decanter. The decanter contains a two-phase mixture. The upper, essentially cyclohexane phase, which contains few products and cobalt, is separated out. The lower acetic phase (2164 g) contains most of the oxidation products and the cobalt. The acetic phase is subjected to distillation under the following conditions:

pressure: 45 kPa and then 30 kPa
temperature: 135° C.

The results collated in the following table are obtained.

TABLE

| Compounds | Recovered as distillation forerun | Recovered in the distillation residue |
|---|---|---|
| cyclohexanone | 205 mmol | 0 mmol |
| cyclohexyl acetate | 22.4 mmol | 0 mmol |
| cyclohexanol | 243.3 mmol | 9 mmol |
| glutaric acid | 0 mmol | 186.4 mmol |
| succinic acid | 0 mmol | 125.3 mmol |
| adipic acid | 0 mmol | 1560 mmol |
| hydroxycaproic acid | 0 mmol | 94 mmol |
| hydroxyadipic acid | 0 mmol | 76.4 mmol |
| butyrolactone | 80.1 mmol | 24.9 mmol |
| valerolactone | 23.7 mmol | 7.9 mmol |
| acetic acid | 1510 9 | <0.1 mmol |

The distillate represents 1860 g and the distillation residue about 300 g.

1000 g of water are added to the distillation residue. The mixture is heated to 85° C. and is then cooled gradually to room temperature.

After filtration and washing with water, 205 g of crude adipic acid are obtained, having an average particle size of 300 $\mu$m and containing (on a weight-for-weight basis):

| (i) succinic acid: | 0.1850% |
|---|---|
| (ii) glutaric acid: | 0.0020% |
| (iii) cobalt: | 0.0080% |
| (iv) water: | 7%. |

Recrystallization of this crude adipic acid from water gives an adipic acid having an average particle size and containing (on a weight-for-weight basis):

| (i) succinic acid: | 0.0002% |
|---|---|
| (ii) glutaric acid: | <0.0001% |
| (iii) cobalt: | <0.0001% |
| (iv) water: | 7%. |

The cobalt catalyst is in the crystallization waters.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method of processing the reaction mixture obtained from the direct oxidation of cyclohexane to adipic acid with oxygen, in an organic solvent and in the presence of a catalyst, said method comprising:
    (a) distilling said reaction mixture to provide (i) a distillate comprising at least some of the most volatile compounds in the reaction mixture and (ii) the distillation residue comprising the diacids formed and the catalyst;
    (b) adding water to the distillation residue to form an aqueous solution; and
    (c) crystallizing the adipic acid from the aqueous solution of the distillation residue.

2. A method according to claim 1, wherein the distillate comprises at least some of the following volatile compounds: unconverted cyclohexane, the organic solvent, cyclohexanone, cyclohexanol, cyclohexyl esters, lactones and water.

3. A method according to claim 1, wherein the reaction mixture obtained from the direct oxidation of cyclohexane to adipic acid undergoes an operation of settling into two liquid phases before the distillation step: an upper phase primarily comprising cyclohexane and a lower phase comprising the organic solvent, the diacids formed, the catalyst and some of the other reaction products, said lower phase being subjected to distillation step (a).

4. A method according to claim 1, wherein the distillation step is carried out at a temperature of from about 25° C. to about 250° C. and at an absolute pressure between about 10 Pa and atmospheric pressure.

5. A method according to claim 2, wherein the distillation step is carried out at a temperature of from about 25° C. to about 250° C. and at an absolute pressure between about 10 Pa and atmospheric pressure.

6. A method according to claim 1, wherein water vapor is introduced into the reaction mixture before or during the distillation step.

7. A method according to claim 1, wherein the water added after the distillation step represents from about 0.01 to about 5 times the weight of the mixture obtained after distillation.

8. A method according to claim 7, wherein the water added after the distillation step represents from about 0.1 to about 3 times the weight of the mixture obtained after distillation.

9. A method according to claim 1, wherein the aqueous solution obtained after the addition of water is subjected to liquid/liquid extraction using a water-immiscible organic solvent.

10. A method according to claim 9, wherein the water-immiscible organic solvent comprises an aliphatic, cycloaliphatic or aromatic hydrocarbon, ester, halogenated hydrocarbon or ether.

11. A method according to claim 10, wherein the water-immiscible organic solvent comprises hexane, cyclohexane, benzene or toluene.

12. A method according to claim 11, wherein the water-immiscible organic solvent comprises cyclohexane.

13. A method according to claim 1, wherein the aqueous solution obtained after the addition of water is heated, to hydrolyze the esters which are still present in said solution, and the cyclohexanol formed by this hydrolysis is removed by azeotropic distillation.

14. A method according to claim 13, wherein the hydrolysis is performed in the presence of a strong acid catalyst.

15. A method according to claim 1, wherein at least some of the compounds distilled are recycled in a further oxidation reaction of cyclohexane to adipic acid, after at least partial elimination of the water contained therein.

16. A method according to claim 1, wherein the organic solvent used in the cyclohexane oxidation comprises an aliphatic carboxylic acid.

17. A method according to claim 16, wherein said aliphatic carboxylic acid is acetic acid.

18. A method according to claim 1, wherein the catalyst comprises cobalt, manganese or a mixture of cobalt and manganese.

* * * * *